United States Patent [19]

Miyazaki et al.

[11] Patent Number: 5,719,027
[45] Date of Patent: Feb. 17, 1998

[54] LABELED COMPLEX AND METHOD OF ANALYSIS THEREWITH

[75] Inventors: Takeshi Miyazaki, Ebina; Tadashi Okamoto; Kazumi Tanaka, both of Yokohama; Toshikazu Onishi, Machida; Tetsuro Fukui, Yokohama; Nobuko Yamamoto, Isehara, all of Japan

[73] Assignee: Canon Kabushiki Kaisha, Tokyo, Japan

[21] Appl. No.: 605,624

[22] Filed: Feb. 22, 1996

Related U.S. Application Data

[62] Division of Ser. No. 191,931, Feb. 4, 1994, abandoned.

[30] Foreign Application Priority Data

Feb. 5, 1993 [JP] Japan ................................ 5-019057

[51] Int. Cl.$^6$ .................................................. G01N 33/533
[52] U.S. Cl. ...................... 435/6; 435/701; 436/501; 436/518; 436/538; 436/546; 436/172; 436/800; 436/805
[58] Field of Search ...................... 435/7.1, 6; 436/501, 436/518, 538, 546, 172, 800, 805

[56] References Cited

U.S. PATENT DOCUMENTS

| | | | |
|---|---|---|---|
| 4,965,183 | 10/1990 | Mee et al. | 430/578 |
| 5,268,486 | 12/1993 | Waggonv et al. | 548/427 |

FOREIGN PATENT DOCUMENTS

| | | |
|---|---|---|
| 0047917 | 3/1982 | European Pat. Off. . |
| 48-52222 | 7/1973 | Japan . |
| 49-18808 | 5/1974 | Japan . |
| 2191674 | 7/1990 | Japan . |

OTHER PUBLICATIONS

F. Hamer, The Cyanine Dyes and Related Compounds, pp. 612–684 (1964).

K. Sauda et al., "Determination of Protein in Human Serum by High Performance Liquid Chromatography with Semiconductor Laser Fluorometric Detection", Analytical Chemistry, vol. 58, No. 13, pp. 2649–2653 (1986).

Kensa To Gijutsu, vol. 16, No. 7 (1988), pp. 614–616.

*Primary Examiner*—Lora M. Green
*Attorney, Agent, or Firm*—Fitzpatrick, Cella, Harper & Scinto

[57] ABSTRACT

A labeled complex formed by combining a labeling agent with a biological substance, where the labeling agent is a trinucleus dye represented by the general formula (I)' or (II)':

$$\text{ring}(Xa)\text{-La-ring}(Xb)\text{-Lb-ring}(Xc) \quad (I)'$$

$$[\text{ring}(Xa)\text{-La-ring}(Xb)\text{-Lb-ring}(Xc)]^{\oplus} \; Y^{\ominus} \quad (II)'$$

where the ring(Xa), ring(Xb), and ring(Xc), which mean rings having Xa, Xb, or Xc respectively, are independently a heterocyclic ring having one to three heteroatoms of oxygen, sulfur, nitrogen, or selenium, the heterocyclic ring being unsubstituted or substituted by any of a substituted or unsubstituted alkyl group, a substituted or unsubstituted aryl group, and a substituted or unsubstituted aralkyl group; La and Lb are independently a methine chain composed of one to six substituted or unsubstituted methine linkage, and one of La and Lb may be omitted to link directly the heterocyclic rings; and $Y^{\ominus}$ represents an anion.

A method of analysis, comprises combining any of the labeled complex with a target substance to be detected, and detecting the target substance optically.

7 Claims, 3 Drawing Sheets

LABELED COMPLEX AND METHOD OF ANALYSIS THEREWITH

This application is a division of application Ser. No. 08/191,931 filed Feb. 4, 1994 now abandoned.

BACKGROUND OF THE INVENTION

1. Field of the Invention

The present invention relates to a labeled complex for microanalysis with red light or near-infrared light. The present invention also relates to a method of analysis employing the above labeled complex.

2. Related Background Art

A trace amount of a substance which has been labeled with a dye or the like gives information such as light scattering, light absorption, fluorescence, or photoacoustic effect on irradiation of laser light. Precise and rapid microanalysis by detecting such information is well known in the field of analysis utilizing laser light.

The laser light sources have been limited conventionally to gas lasers such as argon laser and helium-neon laser. In recent years, however, semiconductor lasers have been developed, which are promising such as the laser light source because of the inexpensiveness, the small size, and the ease of the output control thereof.

In conventional quantitative determination of a trace amount of a biological substance by utilizing ultraviolet light or visible light, background (or blank value) of analysis tends to become high, which is caused by inherent fluorescence (300 to 500 nm) of a natural substance such as flavin, pyridine coenzyme, and serum protein contained usually in specimens. If red or near-infrared light is usable as the light source, such background which is caused by the natural substance can be excluded, thereby enhancing measurement sensitivity for the substance to be detected.

The light emitted from a semiconductor laser is generally in the wavelength region of red to near-infrared light (600 to 830 nm). However, not many dyes emit fluorescent light by light absorption or excitation in such a wavelength region. The typical dyes therefor are binuclear cyanine dyes. An example thereof is a binuclear cyanine dye having a sulfonate group (e.g., Indocyanine Green) used for labeling a plasma protein for high-performance liquid chromatography, which is reported by K. Sauda and T. Imasaka (Anal. Chem. (1986) 58, 2649–2653).

Japanese Patent Application Laid-Open No. 2-191674 discloses detection, by fluorescence, of biological substances labeled with various binuclear dyes having sulfonic groups or a sulfonate groups.

In the detection of the fluorescence, the fluorescent light needs to be spectroscopically separated from the exciting light given to the dye, and to be taken out as the signal. Therefore, the larger the difference between the exciting wavelength and the fluorescent wavelength, the easier is the spectral separation greater the improvement in the S/N ratio.

Conventional lebeled complexes which absorb light of red to near-infrared regions, as exemplified by conventional binuclear cyanine dyes, exhibit difference between the maximum peak wavelength of absorption spectrum and the maximum peak wavelength of fluorescent spectrum (Stokes' shift) of from about 20 nm to about 40 nm, which is insufficient undesirably.

A complex, which is formed by combining the above mentioned dye as the labeling agent with a biological substance such as an antibody, is liable to be denatured by oxidation or crosslinking under action of an environmental factor such as light, heat, humidity, and oxygen in the air. Particularly in water, the denaturation is disadvantageously accelerated by, for example, hydrolysis. Accordingly, the complex is not always useful as the detecting reagent in microanalysis of a component of an organism because of its poor storage stability.

After comprehensive study, the inventors of the present invention found that a dye having a specific structure, as a labeling agent, combined with a biological substance exhibited a relatively large difference of 50 nm to 100 nm between the maximum peak wavelength of the absorption spectrum and the maximum peak wavelength of the fluorescence spectrum, and that the labeled complex was extremely stable. Based on the above findings, the present invention has been accomplished.

SUMMARY OF THE INVENTION

An object of the present invention is to provide a labeled complex which exhibits large Stokes' shift, enables easy spectrum measurement with an improved S/N ratio, and is excellent in storage stability.

Another object of the present invention is to provide a method of analysis by using the above labeled complex.

The labeled complex of the present invention is formed by combining a labeling agent with a biological substance, and is used for detecting optically a target substance after combining the labeled complex selectively with the target substance, the labeling agent being a trinucleus dye represented by the general formula (I) or (II):

where the broken line rings having Xa, Xb, or Xc forms independently substituted or unsubstituted heterocyclic ring having one to three heteroatoms of oxygen, sulfur, nitrogen, or selenium, the heterocyclic ring being unsubstituted or substituted by any of a substituted or unsubstituted alkyl group, a substituted or unsubstituted aryl group, and a substituted or unsubstituted aralkyl group; La and Lb are independently a methine chain composed of substituted or unsubstituted methine linkage, and one of La and Lb may be omitted to link directly the aromatic heterocyclic rings; and $Y^{\ominus}$ represents an anion.

The method of analysis of the present invention employs a labeled complex comprising the above trinucleus dye combined with a biological substance, combining selectively the labeled complex with a target substance to be detected, and detecting optically the target substance.

DETAILED DESCRIPTION OF THE EMBODIMENTS

In the general formula (I) or (II), preferably the broken line rings having Xa, Xb, or Xc are independently a substituted or unsubstituted five- or six-membered heterocyclic ring having one or two nitrogen atoms, or a condensed ring thereof from the viewpoint of the magnitude of the Stokes' shift and ease of spectral separation.

More preferably, the trinucleus dye is a compound represented by the general formula (III) below or an isomer thereof in which the nitrogen atom in the central portion of the formula is at the 5-position instead of the 4-position:

where $r^8$, $r^9$, $r^{10}$, and $r^{11}$ are independently a hydrogen atom, a halogen atom, a substituted or unsubstituted alkyl group, an alkoxy group, a substituted or unsubstituted aryl group, or a substituted or unsubstituted amino group, and $r^8$ and $r^9$ may be bonded to each other to form a substituted or unsubstituted aromatic ring; $r^6$ independently in respective repeating units is absent or is an alkyl-substituted ethylene group, and is linked to $r^8$ or $r^9$ to form a cyclic structure $r^1$ and $r^2$ are independently a substituted or unsubstituted aryl group, or $r^1$ and $r^2$ are linked together to form a substituted or unsubstituted condensed ring; $r^3$, $r^4$, and $r^5$ are independently a hydrogen atom, a substituted or unsubstituted alkyl group, an alkylsulfonate group, a substituted or unsubstituted alkenyl group, a substituted or unsubstituted aryl group, or a substituted or unsubstituted aralkyl group; $X^1$ is an oxygen atom, a sulfur atom, a carbon atom, a nitrogen atom, or a selenium atom, and when $X^1$ is a carbon atom or a nitrogen atom, $X^1$ is bonded to any of hydrogen atoms, a substituted or unsubstituted alkyl groups, a substituted or unsubstituted aryl group or a substituted or unsubstituted aralkyl group; $X^2$ is an oxygen atom, a sulfur atom, or a nitrogen atom, and when $X^2$ is a nitrogen atom, $X^2$ is bonded to any of a hydrogen atom, a substituted or unsubstituted alkyl group, a substituted or unsubstituted aryl, and a substituted or unsubstituted aralkyl group; $X^3$ is an oxygen atom or a sulfur atom; and m and l are independently an integer of from 0 to 3, not being simultaneously 0.

Otherwise preferably the trinucleus dye is a compound represented by the general formula (IV) below or an isomer thereof in which the nitrogen atom in the central portion of the formula is at the 5-position instead of the 4-position:

where $r^{19}$, $r^{20}$, and $r^{21}$ are independently a hydrogen atom, a halogen atom, a substituted or unsubstituted alkyl group, an alkoxy group, a substituted or unsubstituted aryl group, or a substituted or unsubstituted amino group, and $r^{19}$ and $r^{20}$ may be bonded to each other to form a substituted or unsubstituted condensed ring; $r^{12}$, $r^{13}$, $r^{14}$, and $r^{15}$ are independently a substituted or unsubstituted aryl group, or $r^{12}$ and $r^{13}$ or $r^{14}$ and $r^{15}$ are bonded to each other to form a substituted or unsubstituted condensed ring; $r^{16}$, $r^{17}$, and $r^{18}$ are independently a hydrogen atom, a substituted or unsubstituted alkyl group, an alkylsulfonate group, a substituted or unsubstituted alkenyl group, a substituted or unsubstituted aryl group, or a substituted or unsubstituted aralkyl group; $X^4$ and $X^6$ are independently an oxygen atom, a sulfur atom, a carbon atom, a nitrogen atom, or a selenium atom, and when $X^4$ or $X^6$ is a carbon atom or a nitrogen atom, $X^4$ or $X^6$ is linked to any of hydrogen atoms, a substituted or unsubstituted alkyl group, a substituted or unsubstituted aryl group, or a substituted or unsubstituted aralkyl group; $X^5$ is an oxygen atom, a sulfur atom, or a nitrogen atom, and when $X^5$ is a nitrogen atom, $X^5$ is bonded to any of a hydrogen atom, a substituted or unsubstituted alkyl group, a substituted or unsubstituted aryl group, and a substituted or unsubstituted aralkyl group; $Z^\ominus$ represents an anion; and y is an integer of 0, 1, or 2.

The biological substance may be an antibody, an antigen, or an nucleic acid.

The labeled complex of the present invention gives a large Stokes' shift of as high as 50 to 100 nm in optical analysis of a target substance with a semiconductor laser, thereby enabling detection of the target substance with a high S/N ratio. This labeled complex has excellent storage stability and therefore is highly useful as an analysis agent.

The present invention is described below more specifically.

In the present invention, a trinucleus dye is used as the labeling agent. The trinucleus dyes are known as photosensitive compounds for photosensitive materials, and described in literature, e.g., Japanese Patent Application Laid-Open No. 48-52222, Japanese Patent Publication No. 49-18808, "The Cyanine Dyes and Related Compounds" written by Frences M. Hamer, pp. 612–684 (1964), etc. The trinucleus dyes, which are useful in silver salt photography, are not known at all to be useful for a labeling agent to give fluorescence to a biological substance. It was found by the inventors of the present invention that a trinucleus dye having a specific structure is highly useful in optical analysis with a semiconductor laser, and based on this finding, the present invention has been completed.

The preferred trinucleus dye in the present invention has a structure comprising three heterocyclic rings linked by at least one methine or polymethine chain (as represented by the general formula (I)) or a structure of ionized salt form thereof (as represented by the general formula (II)).

Xa, Xb, and Xc independently constitute a nuclear cyclic structure (a heterocyclic ring). The cyclic structure is a heterocyclic ring having a heteroatom, preferably a five- or six-membered ring having a nitrogen atom.

The heterocyclic ring does not include a cyclic structure which is formed by simple bridging between two or more carbon atoms in the polymethine chain, because the cyclic structure bridged to the methine chain is generally a carbon ring, and such a structure does not contribute to the increase of the Stokes' shift.

The three heterocyclic rings of the trinucleus dye are linked by methine chains represented by La and Lb which are composed of one to six substituted or unsubstituted methine units (one methine unit is also included into the methine chain for convenience although one methine unit does not make a chain), thereby the three heterocyclic ring forming a resonance system. In the trinucleus dye, one of La and Lb may be omitted to link the two aromatic heterocyclic rings directly. The number of the methine unit in the methine chain may be even or odd. When the number is even, the heterocyclic rings are linked to the methine chain at the both chain ends respectively through a single bond, or through a double bond, whereas, when the number is odd, the aromatic rings are linked to the methine chain through a single bond at one end of the chain and through a double bond at the other end of the chain. The methine chain is preferably composed of two methine units which has a double bond on each end. The number of the repeating units in the methine chain is preferably not more than 3, namely not more than six methine units. With a longer methine chain than six, the absorption wavelength becomes 900 nm or longer disadvantageously, and simultaneously the compound itself becomes unstable. If the methine chains La and Lb are both absent, the aromatic heterocyclic rings are directly linked. In this case, the absorption wavelength becomes undesirably shorter than 600 nm.

The compound represented by the general formula (I) may take an ionized salt structure as shown by the general formula (II). The salt form of the compound is selected when ionic bonding interaction is desired between the compound and the biological substance. In the general formula (II), $Y^{\ominus}$ represents an anion which is the same as the one in the general formula (IV) described later.

Examples of the heterocyclic rings are shown below:

In the above formulas, Ra, Rb, Rc, and Rd are independently a hydrogen atom or substituents. The substituents include alkyl groups, halogen atoms such as I, Br, and Cl, alkoxy groups, alkylsulfonate groups, and alkenyl groups.

Examples of La and Lb are shown below.

In the formulas, Re and Rf include the above groups mentioned for Ra, Rb, Rc, and Rd and additionally aryl groups and aralkyl groups; and p is an integer of 0, 1, 2, and 3.

Typical compounds having the above constitution includes cyanine dyes, merocyanine dyes, rhodacyanine dyes, oxonol dyes, styryl dyes, and base styryl dyes.

Preferred structures of the dyes include the structures represented by the general formulas (III) and (IV), of which the ones represented by the general formula (III) are more preferable.

The alkyl group in the present invention is preferably those having 1 to 12 carbons such as methyl, ethyl, n-propyl, isopropyl, n-butyl, sec-butyl, isobutyl, t-butyl, n-amyl, t-amyl, n-hexyl, n-octyl, t-octyl, and so on, of which linear or branched alkyl groups having one to four carbons are more preferable.

The substituted alkyl group includes 2-hydroxyethyl, 2-methoxyethyl, 2-ethoxyethyl, methoxymethyl,3-hydroxypropyl, 3-methoxypropyl, 3-ethoxypropyl, 3-chloropropyl, 3-bromopropyl, 3-carboxypropyl, etc. The alkoxy group is the same as the above alkyl group in the carbon number and the structure, including methoxy, ethoxy, propoxy, etc.

The substituted or unsubstituted aryl group includes phenyl, tolyl, xylyl, biphenyl, aminophenyl, α-naphthyl, β-naphthyl, anthranyl, pyrenyl, methoxyphenyl, dimethoxyphenyl, trimethoxyphenyl, ethoxyphenyl, diethoxyphenyl, chlorophenyl, dichlorophenyl, trichlorophenyl, bromophenyl, dibromophenyl, tribromophenyl, ethylphenyl, diethylphenyl, nitrophenyl, aminophenyl, dimethylaminophenyl, diethylaminophenyl, dibenzylaminophenyl, dipropylaminophenyl, morpholinophenyl, piperidinylphenyl, piperazinophenyl, diphenylaminphenyl, acetylaminophenyl, benzoylaminophenyl, acetylphenyl, benzoylphenyl, cyanophenyl, sulfonatephenyl, carboxylatephenyl, etc.

The alkenyl group in the present invention has preferably 1 to 10 carbons, more preferably 1 to 6 carbons, exemplified by vinyl, propenyl, butenyl, pentenyl, hexenyl, heptenyl, octenyl, and dodecenyl.

The substituted or unsubstituted aralkyl group has preferably 7 to 19 carbons, more preferably 7 to 15 carbons, exemplified by benzyl, phenethyl, tolylmethyl, hydroxybenzyl, 2-hydroxy-3-methylbenzyl, and 2-hydroxy-3-t-butylbenzyl.

The compounds (labeling agent) represented by the general formula (III) or (IV) are generally slightly soluble in water. Therefore, to impart water-solubility to these compounds, one or more of the groups of $r^1$ to $r^{21}$ need to contain a polar group such as hydroxyl, alkylhydroxy, sulfonate, alkylsulfonate, carboxylate, alkylcarboxylate, tetra-ammonium salt, and other known groups. However, in the case where the biological substance as the carrier of the dye is a water-soluble high-molecular substance, the labeled complex as a whole is water-soluble even if the labeling agent to be combined is hardly soluble in water, therefore the aforementioned polar group being not always necessary. Such a biological substance is exemplified by nucleic acids, antibodies, glycoproteins, and the like, which will be explained later.

The groups $r^1$ to $r^5$, or the groups $r^{12}$ to $r^{15}$ preferably have at least one reactive group to enable the formation of a covalent bond between the compound of the general formula (III) or (IV) and the biological substance as the carrier. However, when the labeling compound is intercalated into a biological substance, or is combined therewith by ionic bonding, the reactive group is not necessarily required.

The reactive group has the reactive sites, including isocyanate, isothiocyanate, succinimide ester, sulfosuccinimide ester, imide ester, hydrazine, nitroaryl halide, bipyridine disulfide, maleimide, thiophthalimide, acid halide, sulfonyl halide, aziridine, azidonitrophenyl, azidoamino, 3-(2-pyridyldithio)propionamide, and other known reactive groups. To exclude steric hindrance between the labeling agent and the biological substance, the reactive sites may have a spacer portion, e.g., where q is an integer of from 0 to 6.

Of the above reactive groups, particularly preferred are isocyanate, sulfosuccinimide ester, succinimide ester, maleimide, etc.

In the general formula (IV), $Z^{\ominus}$ is an anion, including chloride ion, bromide ion, iodide ion, perchlorate ion, benzenesulfonate ion, p-toluene-sulfonate ion, methylsulfate ion, ethylsulfate ion, propylsulfate ion, tetrafluoroborate ion, tetraphenylborate ion, hexafluorophosphate ion, benzenesulfinate ion, acetate ion, trifluoroacetate ion, propionate ion, benzoate ion, oxalate ion, succinate ion, malonate ion, oleate ion, stearate ion, citrate ion, hydrogendiphosphate ion, dihydrogenphosphate ion, pentachlorostannate ion, chlorosulfonate ion, fluorosulfonate ion, trifluoromethanesulfonate ion, hexafluoroantimonate ion, molybdate ion, tungstate ion, titanate ion, zirconate ion, etc.

Specific examples of the general formula (III) and (IV) are shown below (Compound Nos. 1 to 12), but the labeling agent is not limited thereto.

(1)

-continued (2)

(3)

(4)

(5)

(6)

(7)

(8)

-continued (9)

(10)

(11)

(12)

Table 1 shows maximum absorption wavelengths (nm) and maximum fluorescence wavelength (nm) (in methanol) of the above dye examples.

TABLE 1

| Number | Maximum absorption wavelength (nm) | Maximum fluorescence wavelength (nm) |
|---|---|---|
| 1 | 652 | 735 |
| 2 | 670 | 755 |
| 3 | 620 | 715 |
| 4 | 636 | 725 |
| 5 | 695 | 775 |
| 6 | 604 | 680 |
| 7 | 778 | 840 |
| 8 | 608 | 675 |
| 9 | 629 | 675 |
| 10 | 651 | 710 |
| 11 | 602 | 660 |
| 12 | 785 | 840 |

The labeling agent of the present invention absorbs light in the red to near-infrared region (600 to 900 nm), and the molar absorption coefficient ε is in the range of from 20,000 to 100,000 l/mol.cm. The labeling agent emits fluorescent light with a maximum fluorescence wavelength shifting to the longer wavelength side by about 50 to 100 nm from the maximum absorption wavelength.

The trinucleus dye, which is the basic skeleton of the aforementioned labeling agent, is described in literature, e.g., "The Cyanine Dyes and Related Compounds", written by Frences M. Hame, pp. 612–684 (1964), etc., and can be produced by any suitable method. The functional group to form a covalent bond with a biological substance can be introduced to the compound, for example, by reacting a succinimide-introducing agent (e.g., sodium N-hydroxysulfosuccinimide) with the trinucleus cyanine carboxylate salt by use of a condensing agent (e.g., N,N'-dicyclohexylcarbodiimide).

The labeling agent in the present invention is combined with a biological substance. The biological substance as the carrier is selected for an individual substance to be analyzed or detected. Selective detection of a substance can be made by using a biological substance which has biological specificity to the substance to be detected. The biological substance herein includes natural or synthetic peptides, proteins, enzymes, sugars, lectins, viruses, bacteria, nucleic acids, DNAs, RNAs, antigens (including recombinant antigens), antibodies, and so forth. Further, particularly useful substances clinicopathologically as the carrier are as follows: immunoglobulins, e.g., IgG, IgM, IgE, etc.; serum proteins, e.g., complements, CRP, ferritin, $\alpha_1$-microglobulin, $\beta_2$-microglobulin, etc., and antibodies thereof; tumor markers, e.g., $\alpha$-fetoprotein, carcinoembryonic antigen (CEA), prostatic acidic phosphatase (PAP), CA19-9, CA-125, etc., and antigens thereof; hormones, e.g., luteinizing hormone (LH), follicle-stimulating hormone (FSH), human chorionic gonadotropin (hCG), estrogen, insulin, etc, and antibodies thereof; virus infection-related substances, e.g., HBV-related antigen (HBs, HBe, HBc), HIV, ATL, etc., and antibodies thereof; bacteria, e.g., Corynebacterium diphtheriae, Clostridium botulinum, mycoplasma, Treponema pallidum, etc., and antibodies thereof; protozoa, e.g., Toxoplasma, Trichomonas, Leishmania, Tripanosoma, Plasmodium, etc. and antigens thereof; antiepileptics, e.g., phenytoin, phenobarbital, etc.; cardiovascular medicines, e.g., quinidine, digoxinin, etc.; antiasthmatics e.g., theophylline, etc.; medicines such as antibiotics, e.g., chloramphenicol, gentamycin, etc. and antigens thereof; enzymes, and exotoxins (e.g., streptolysin O), and antibodies thereof. The biological substance as the carrier is suitably selected which undergoes a reaction such as antigen-antibody reaction with the substance to be detected in the specimen.

The labeling agent in the present invention may be combined with (or immobilized on) a biological substance such as the above-mentioned physiologically active substance by a known method, including (i) ionic bonding, (ii) physical adsorption, and (iii) covalent bonding as below.

In the ionic bonding, a positively charged labeling agent is bonded to a biological substance such as protein, DNA, RNA, and the like.

In the physical adsorption, the lipophilic portion of the labeling substance is bonded to the lipophilic portion of protein by a hydrophobic bond.

The ionic bonding and the physical adsorption exhibit low bond strength between the labeling agent and the biological substance, although the bond can be formed readily by a simple bonding reaction procedure.

In the covalent bonding, on the other hand, at least one of the labeling agent of the biological substance has a highly reactive functional group, through which the both substances are bonded by covalent bonding to form a strong bond. The functional group capable of forming the covalent bond of the biological substance includes free amino groups, a hydroxyl group, a phosphoric acid group, a carboxyl group, a sulfhydryl group of cysteine, an imidazole group of histidine, a phenol group of tyrosine, a hydroxyl group of serine and threonine, and so forth.

These functional groups react a diazonium salt, an acid amide, an isocyanate, an active alkyl halide, an active ester group. By introducing such a group into the labeling agent, the dye can be combined with the biological substance in a suitable method. On the other hand, the conformation of the biological substance, especially of the substance of organism origin, is held by relatively weak bonds such as hydrogen bonds, hydrophobic bonds, and ionic bonds, being liable to be destroyed. Therefore, the immobilization of the labeling agent is desirably carried out under mild conditions without treatment at high temperature and without using a strong acid or strong alkali.

In one method of the immobilization reaction under mild conditions, a bifunctional crosslinking agent is useful which reacts with the labeling agent and with the biological substance. The bifunctional crosslinking agent includes carbodiimides represented by the general formula: R—N=C=N—R', dialdehydes represented by the general formula: CHO—R—CHO, diisocyanates represented by the general formula O=C=N—R—N=C=O, and the like (where R and R' are independently an alkyl group, an aryl group, an alkylaryl group, or an arylalkyl group, which may be substituted.).

The method of analysis is described below in which a specific substance is detected by use of the labeled complex formed from a labeling agent and a biological substance.

A target substance (or an object to be detected), which is a kind of a cell or a microorganism, can be detected as follows. The labeled complex is allowed to combine with a cell or a specific substance on the surface of the microorganism which is complementary to the biological substance of the labeled complex, the bonding being formed specifically through a specific bond such as an antigen-antibody bond, a hydrogen bond between nucleic acids, and the like. Then the quantity of the antigen, the antibody, the nucleic acids, etc. is measured by the fluorescence intensity of the system.

The fluorescence intensity can be measured by a fluorophotometer or a fluorescence microscope. Otherwise, individual cells or microorganisms are passed through an excitation light-irradiation region in a flow system at a high speed, the fluorescent light being measured and the data being treated statistically according to flow cytometry.

As the excitation light source, semiconductor lasers are useful which have an emission wavelength in a red to near-infrared region, since the labeled complex of the present invention is excited by light of the red to near-infrared region (600 to 900 nm).

Since the labeled complex of the present invention exhibits a larger Stokes' shift, two or more fluorescent substances emitting different wavelengths of fluorescence can be measured respectively with irradiation of one wavelength of laser in such a manner that one target substances is labeled with a labeled complex of the present invention and another target substance is labeled with a conventional binuclear labeling agent such as binuclear cyanine dyes and binuclear rhodamine dyes exhibiting smaller Stokes' shift.

Furthermore, a dissolved component such as a component contained in body fluid such as serum can be detected with such a labeled complex, for example as follows.

In the case where analysis is carried out by utilizing antigen-antibody reaction, a labeled complex formed by reaction of the labeling agent with an antigen (or an antibody) is subjected to antigen-antibody reaction with a target antibody (or antigen, if the labeling agent is bonded to an antibody), and the antigen-antibody reaction complex (B=bonded type) is separated (B/F separation) from the complex not bonded to the antibody (F=free type) (or antigen), and thereafter the bonded type (B) is determined by the intensity of emitted fluorescence. This technique utilizing the antigen antibody reaction is described in detail in publication: "Kensa to Gijutsu (Inspection and Technique)", Vol. 16, No. 7 (1988).

Figure 1:
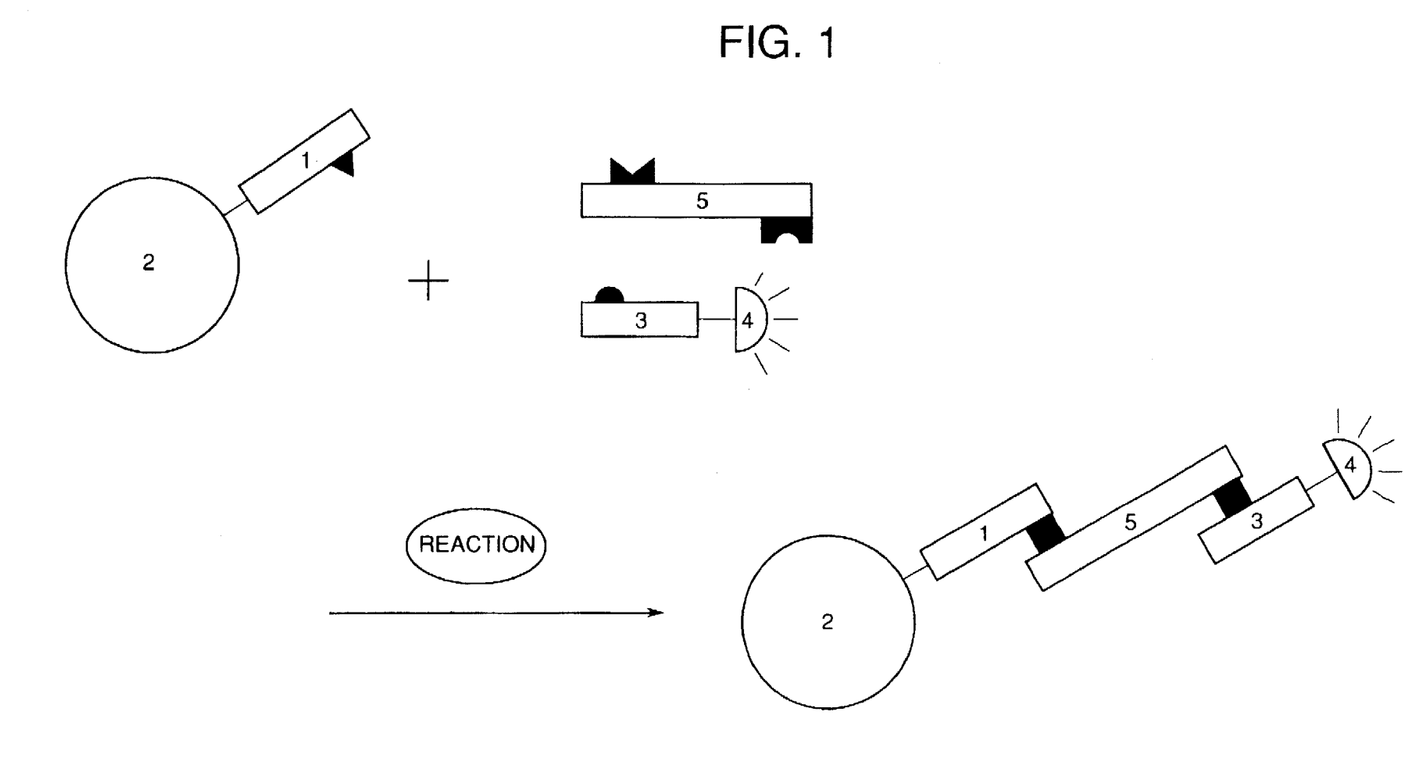
FIG. 1 illustrates schematically the principle of detecting a target substance by a sandwich assay method employing a probe carrying a labeling agent of the present invention.

The B/F separation in the detection can be facilitated by a sandwich assay method by employing fine particles as an immobilizing carrier. The principle thereof is illustrated schematically in FIG. 1. A first probe 1 (e.g., nucleic acid, antigen, antibody, etc.) which is capable of specifically bonding to the target substance 5, and a second probe 3 are selected. The first probe is immobilized on a immobilizing carrier 2, and the second probe is bonded to the labeling agent 4 to form a labeled complex. The target substance in a measured sample undergoes reaction to bond the first probe and the second probe with interposition of the target substance, thereby the labeled complex being bonded to the immobilizing carrier. After the reaction, unbonded labeled complex (F) is subjected to B/F separation, and the quantity of the labeled complex on the carrier is determined by fluorometry.

In consideration of sensitivity of the detection, it is desirable that the labeled complex has two or more moles of the labeling agent bonded to one mole of the biological substance (probe). Therefore, in a mixed system in which the labeled complex having two or more moles of labeling agent and the labeled complex having one mole of the labeling agent are mixed, the molar ratio of the labeling agent to the biological substance is preferably not less than 1.5:1, more preferably not less than 2:1. When the biological substance is antigen or the like, more than one molecule of the labeling agent can readily be bonded thereto. When the biological substance is a nucleic acid, more than one primary amino group is introduced to one molecule of the nucleic acid, and then the labeling agent is bonded thereto, thus the measurement sensitivity being raised corresponding to the number of the introduced amino groups (namely the number of the introduced labeling agent).

In the above fluorescence detection, the detection sensitivity can be raised by addition of a surfactant to increase the fluorescence intensity. The surfactant includes anionic surfactants, nonionic surfactants, cationic surfactants, and amphoteric surfactants. The surfactant is added preferably in an amount ranging from about 0.01 to about 1.0% by weight based on the measurement solvent. For example, addition of Tween 20, a nonionic surfactant, in an amount of 0.1% increases the fluorescence intensity by a factor of about five.

The present invention is described below more specifically.

<Stokes' Shift of Labeled complex>

EXAMPLE 1

Anti-human CRP sheep serum (IgG fraction) (made by Cooper Biomedical Inc.) was diluted to a concentration of 0.5 mg/ml with a phosphate buffer solution (pH: 8.0) to prepare an antibody solution. To 7 ml of this antibody solution, were added 0.3 mg of the aforementioned labeling agent No. 4, and 0.08 g of 1-ethyl-3-(3-dimethylaminopropyl)-carbodiimide hydrochloride (made by Dojin Kagaku K.K., hereinafter referred to as "WSC"). The mixture was allowed to react at room temperature for 3 hours to form a labeling agent-antigen complex. The resulting labeling agent-antigen complex was separated and purified from the unreacted matter by a gel filtration chromatography with a Sepharose 6B column.

Figure 2:
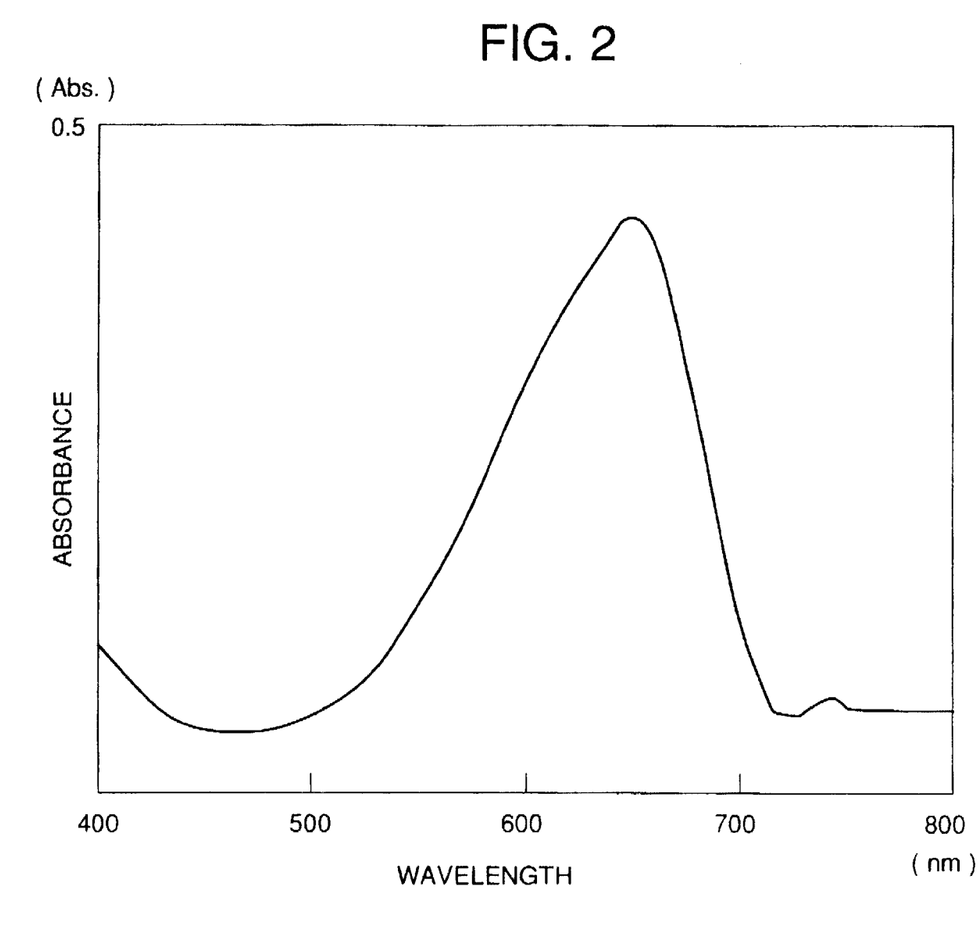
FIG. 2 shows an absorption spectrum of the labeling agent-antigen complex obtained in Example 1 of the present invention.
Figure 3:
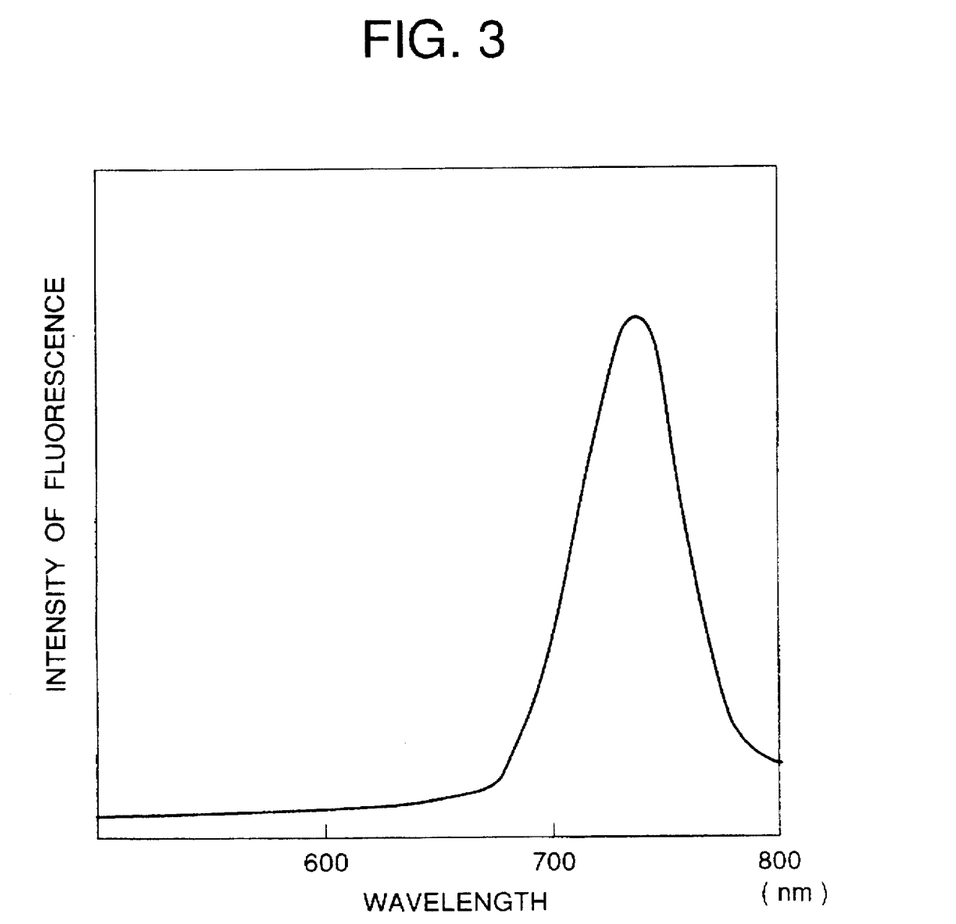
FIG. 3 shows a fluorescence spectrum of the labeling agent-antigen complex obtained in Example 1 of the present invention.

FIG. 2 shows the absorption spectrum of the obtained labeling agent-antibody complex, and FIG. 3 shows the fluorescence spectrum thereof. The maximum absorption wavelength ($\lambda_{max}$) was 641 nm, and the maximum fluorescence wavelength ($\lambda_{em}$) was 730 nm, the difference of the wavelengths (Stokes' shift) being 89 nm. Some discrepancies are found between the labeling agent itself and the labeled complex in the maximum absorption wavelength and the maximum fluorescence wavelength. This is considered to be due mainly to the effect of the measurement solvent. (The same is true in the following Examples.)

In this labeling agent-antibody complex, the ratio of the bonded labeling agent to the bonded antibody (in moles) was estimated to be 1.9:1 from the absorbances at wavelengths $\lambda=641$ nm and $\lambda=280$ nm.

EXAMPLE 2

Anti-human HCG monoclonal antibody (made by ZyMED Lab. Inc.) was diluted to a concentration of 0.25 mg/ml with a phosphate-buffered saline (PBS, pH: 7.2) to prepare a monoclonal antibody solution. To 7 ml of this antibody solution, was added 0.2 mg of the aforementioned labeling agent No. 2. The mixture was allowed to react at 20° C. for 6 hours with stirring to form a labeling agent-antigen complex. The resulting labeling agent-antigen complex was separated and purified from the unreacted matter by gel filtration chromatography with a Sepharose 6B column.

The resulting labeling agent-antibody complex had the maximum absorption wavelength ($\lambda_{max}$) of 674 nm, and the maximum fluorescence wavelength ($\lambda_{em}$) of 755 nm, the difference of the wavelengths (Stokes' shift) being 81 nm.

In this labeling agent-antibody complex, the ratio of the bonded labeling agent to the bonded antibody (in moles) was estimated to be 2.2:1 from the absorbances at wavelengths $\lambda=674$ nm and $\lambda=280$ nm measured by UV-visible spectroscopy.

EXAMPLE 3

A lectin solution was prepared by diluting lectin-concanavalin A (made by E.Y. Laboratories Co.) to a concentration of 0.2 mg/ml with a phosphate buffer solution (pH: 8.2). To 10 ml of this lectin solution, was added 0.2 mg of the aforementioned labeling agent No. 3. The mixture was allowed to react at room temperature for 3 hours. The resulting labeling agent-lectin complex was separated and purified from the unreacted matter by a gel filtration chromatography with a Sepharose 6B column.

The resulting labeling agent-lectin complex had the maximum absorption wavelength of 625 nm, and the maximum fluorescence wavelength of 720 nm, the difference of the wavelengths (Stokes' shift) being 95 nm.

In this labeling agent-lectin complex, the ratio of the bonded labeling agent to the bonded lectin (in moles) was estimated to be 3.7:1 from the absorbances at wavelengths $\lambda=625$ nm and $\lambda=280$ nm measured by UV-visible spectroscopy.

EXAMPLE 4

A DNA solution was prepared by dissolving 0.1 mg of single-stranded DNA, M13mp18 (7249 base) (made by Takara Shuzo Co., Ltd.) in 5 ml of 5 mmol phosphate buffer solution (pH: 6). Separately, a dye solution was prepared by dissolving 0.1 mg of the aforementioned labeling agent No. 2 in 5 ml of distilled water. To this dye solution, the above DNA solution (5 ml) was slowly added dropwise with stirring, and the mixture was further stirred at room temperature for 2 hours to form a DNA-labeling agent complex.

To the above DNA-labeling agent complex solution, 40 ml of ethanol was added to precipitate the DNA-labeling agent complex. The precipitate was collected by filtration, and was washed with ethanol several times. The washed DNA-labeled complex was again dissolved in 2 ml of the above phosphate buffer solution (pH: 6). The amount of the labeling agent bonded to the DNA was estimated to be 0.5 μg for 1 μg of DNA from the absorbances at the wavelengths of $\lambda=668$ nm and $\lambda=260$ nm.

The resulting DNA-labeling agent complex had the maximum absorption wavelength of 668 nm, and the maximum fluorescence wavelength of 755 nm, the difference of the wavelengths (Stokes' shift) being 87 nm.

EXAMPLE 5

A 20-meric oligonucleotide was synthesized which had a base sequence partially complementary to the base sequence of a model target nucleic acid, M13mp18ss DNA, by means of an automatic DNA synthesizer (Model 381A, made by ABI Co.). To the 5'-terminal of the above oligonucleotide, a primary amino group was introduced by using an N-MMT-hexanol amine linker (made by Milligenne Co.) in place of a usual amidide reagent. The cutting out from the CPG carrier, deprotection (including monomethoxytrityl group as the protection group for a primary amino group), and purification by high-performance liquid chromatography were conducted according to the conventional protocol.

200 μg of the above nucleotide, 100 μl of 1M sodium carbonate buffer solution (pH:9.0), and 700 μl of water were mixed to form a solution. Thereto, a preliminarily prepared solution of 2 mg of the aforementioned labeling agent No. 3 in 200 μl of dimethylformamide was added gradually with stirring. The mixture was allowed to react at room temperature for 24 hours, whereby the peak of the nucleic acid in high-performance liquid chromatography decreased and a new peak emerged which had both the absorption of the nucleic acid and the absorption of the labeling agent. The reaction mixture was roughly purified with a gel filtration column (NAP-50, made by Pharmacia Co.), and further purified by high-performance liquid chromatography. Thereby, a nucleic acid-labeling agent complex was obtained in a yield of 175 μg. The molar ratio of the nucleic acid to the labeling agent in the obtained labeled complex was 1:1, since one amino group was introduced to one molecule of the nucleic acid.

The maximum absorption wavelength of the resulting DNA-labeling agent complex was 625 nm, and the maximum fluorescence wavelength thereof was 720 nm, the difference of the wavelengths (Stokes' shift) being 95 nm.

EXAMPLE 6

A 20-meric oligonucleotide was synthesized which had a base sequence partially complementary to the base sequence of a model target nucleic acid, M13mp18ss DNA, by means of an automatic DNA synthesizer (Model 381A, made by ABI Co.). To the 5'-terminal of the above 20-meric oligonucleotide, 10 monomer units of a deoxyuridylic acid derivative having a primary amino group was introduced by using a deoxyuridylic acid derivative monomer having the following formula:

in place of a usual amidide reagent similarly by means of the automatic DNA synthesizer. The cutting out from the CPG carrier, deprotection (including trifluoroacetyl group as the protection group for a primary amino group), and purification by high-performance liquid chromatography were conducted in a conventional protocol.

200 μg of the above nucleotide having primary amino groups, 100 μl of 1M sodium carbonate buffer solution (pH: 9.0), and 700 μl of water were mixed to form a solution. Thereto, a preliminarily prepared solution of 2 mg of the aforementioned labeling agent No. 3 in 200 μl of dimethylformamide was added gradually with stirring. The mixture was allowed to react at 40° C. for 24 hours, whereby the peak of the nucleic acid in high-performance liquid chromatography decreased and a new peak emerged which had both the absorption of the nucleic acid and the absorption of the labeling agent. The reaction mixture was roughly purified with a gel filtration column (NAP-50, made by Pharmacia Co.), and further purified by high-performance liquid chromatography. Thereby, a nucleic acid-labeling agent complex was obtained in a yield of 350 μg. The absorbance of the nucleic acid-labeling agent complex at 628 nm was about 10 times that of the nucleic acid-labeling agent complex in Example 5. This is ascribable to the molar ratio of the nucleic acid to the labeling agent of 1:10 resulting from the introduction of 10 primary amino groups per mole of the nucleic acid in this Example in comparison with that ratio of 1:1 in Example 5.

The resulting DNA-labeling agent complex had the maximum absorption wavelength of 628 nm, and the maximum fluorescence wavelength of 720 nm, the difference of the wavelengths (Stokes' shift) being 92 nm.

EXAMPLE 7

To 7 ml of the antibody solution prepared in Example 1, were added 0.3 mg of the aforementioned dye No. 12, and 0.08 g of WSC. The mixture was allowed to react at room temperature for 3 hours to form a labeling agent-antibody complex. The resulting complex was separated and purified by gel filtration chromatography with a Sepharose 6B column.

The resulting labeling agent-antibody complex had the maximum absorption wavelength ($\lambda_{max}$) of 780 nm and the maximum fluorescence wavelength ($\lambda_{em}$) of 835 nm, the difference of the wavelengths (Stokes' shift) being 55 nm.

The molar ratio of the bonded labeling agent to the bonded antibody of the labeling agent-antibody complex was estimated to be 1.9:1 from the absorbances at wavelengths $\lambda=780$ nm and $\lambda=280$ nm measured by UV-visible spectroscopy.

Comparative Example 1

A known typical binucleus dye binucleus cyanine dye) was used which had the chemical structure shown below:

To 7 ml of the antibody solution prepared in Example 1, were added 0.3 mg of the above dye, and 0.08 g of WSC. The mixture was allowed to react at room temperature for 3 hours to form a labeling agent-antibody complex. The resulting labeling agent-antibody complex was separated and purified by gel filtration chromatography with a Sepharose 6B column.

The obtained labeling agent-antibody complex had the maximum absorption wavelength ($\lambda_{max}$) of 785 nm and the maximum fluorescence wavelength ($\lambda_{em}$) of 815 nm, the difference of the wavelengths (Stokes' shift) being as small as 30 nm.

The molar ratio of the bonded labeling agent to the bonded antibody was estimated to be 1.5:1 from the absorbances at wavelengths $\lambda=785$ nm and $\lambda=280$ nm measured by UV-visible spectroscopy.

Comparative Example 2

A known typical binucleus cyanine dye was used which has the chemical structure shown below having a bridge of a polymethine chain:

To 7 ml of the antibody solution prepared in Example 1, were added 0.3 mg of the above dye, and 0.08 g of WSC. The mixture was allowed to react at room temperature for 3 hours to form a labeling agent-antibody complex. The resulting labeling agent-antibody complex was separated and purified by gel filtration chromatography with a Sepharose 6B column.

The obtained labeling agent-antibody complex had the maximum absorption wavelength ($\lambda_{max}$) of 782 nm and the maximum fluorescence wavelength ($\lambda_{em}$) of 810 nm, the difference of the wavelengths (Stokes' shift) being as small as 28 nm.

The molar ratio of the bonded labeling agent to the bonded antibody was estimated to be 1.7:1 from the absorbances at wavelengths $\lambda=782$ nm and $\lambda=280$ nm measured by UV-visible spectroscopy.

As shown in Examples 1 to 7, the labeled complex having the trinucleus dye of the present invention exhibits the Stokes' shift (difference between the maximum absorption wavelength and the maximum fluorescence wavelength) of not less than 50 nm, whereas the labeled complex derived from the dye having absorption at red to near-infrared region typified by the binucleus cyanine dye employed in Comparative Examples 1 and 2 and the specific rhodamine dye exhibits the Stokes' shift as small as 20 to 40 nm. The labeled complex of the present invention can be readily detected by spectroscopy, and enables detection of target substance with a high S/N ratio.

<Storage Stability of Labeled complex>

The storage stability of the labeled complexes was tested as below.

Each of the labeled complexes prepared in Examples 1 to 7 and Comparative Examples 1 and 2 was dissolved respectively in 10 mmol phosphate buffer solution (pH: 7.2) at a predetermined concentration. The labeled complex solution was stored at 10° C. for 3 days in the dark.

The light absorbance and the fluorescence intensity of each of the solution were measured at the start and the end of the storage test. The relative values of the absorbance and of the fluorescence intensity at the end of the storage test were shown by the ratios to those at the start of the storage test (the values at the start being taken to be 100).

TABLE 2

| | Storage Stability of Labeled complex | | |
|---|---|---|---|
| | Concentration (µg/ml) | Absorbance after storage (100 at start) (wavelength nm) | Fluorescence intensity after storage (100 at start) (wavelength nm) |
| Example | | | |
| 1 | 0.6 | 94.2 (641) | 95 (730) |
| 2 | 0.7 | 92.8 (674) | 93 (755) |
| 3 | 0.7 | 95.1 (625) | 98 (720) |
| 4 | 0.6 | 94.5 (688) | 94 (755) |
| 5 | 0.7 | 93.9 (625) | 92 (720) |
| 6 | 0.7 | 92.8 (628) | 94 (720) |
| 7 | 0.7 | 90.5 (780) | 90 (835) |

TABLE 2-continued

Storage Stability of Labeled complex

| | Concentration (μg/ml) | Absorbance after storage (100 at start) (wavelength nm) | Fluorescence intensity after storage (100 at start) (wavelength nm) |
|---|---|---|---|
| Comparative Example | | | |
| 1 | 0.7 | 70.3 (785) | 68 (815) |
| 2 | 0.7 | 72.8 (782) | 73 (810) |

As shown in Table 2, the labeled complexes of the present invention changed less in the absorbance and the fluorescence intensity in water than those of Comparative Examples, which shows the excellent storage stability of the labeled complexes of the present invention. The labeled complexes of the present invention exhibited Stokes' shift (difference between the maximum absorption wavelength and the maximum fluorescence wavelength) of not less than 50 nm as shown in Examples 1 to 7. On the contrary, the labeled complex derived from the dye having absorption at red to near-infrared region typified by the binucleus cyanine dye employed in Comparative Examples 1 and 2 and the specific rhodamine dye exhibited the Stokes' shift as small as 20 to 40 nm.

As described above, the labeled complex of the present invention exhibits a larger Stokes' shift, and therefore the fluorescence is readily separated from the exciting light in detection of the labeled substance with a higher S/N ratio. Accordingly, the detection sensitivity is raised even when the specificity of the biological substance of the labeled complex to the target substance is the same. Furthermore, if a labeled complex exhibiting a smaller Stokes' shift (e.g., a cyanine complex) is combined with the one of the present invention, two kinds of fluorescence signal can be detected with one wavelength of exciting light such as laser. Additionally, the labeled complex of the present invention is stable and does not deteriorate in the fluorescence-emitting property even when stored as an aqueous solution, so that the complex provide reagents with excellent stablity under storage for the application to microanalysis.

What is claimed is:

1. A process for detecting a biological substance of interest in a sample comprising the steps of:

(i) providing a labeled binding partner which specifically binds to the biological substance of interest;

(ii) complexing the labeled binding partner with the sample containing the biological substance of interest to form a labeled complex;

(iii) separating the unbound labeled binding partner from the labeled complex formed in step (ii); and (iv) irradiating the labeled complex with a semiconductor laser having an emission wavelength within 600 to 900 nm to measure the strength of fluorescent light emitted by the label, thereby measuring the presence and/or amount of the biological substance of interest in the sample;

wherein the label is a trinucleus dye represented by the following general formula of either (I) or (II)

where the broken line rings having Xa, Xb, or Xc are independently a heterocyclic ring having one to three heteroatoms of oxygen, sulfur, nitrogen, or selenium, the heterocyclic ring being unsubstituted or substituted by any of a substituted or unsubstituted alkyl group, a substituted or unsubstituted aryl group, and a substituted or unsubstituted aralkyl group; La and Lb are independently a methine chain composed of one to six substituted or unsubstituted methine linkages, and one of La and Lb may be omitted to link directly the heterocyclic rings; and Y represents an anion.

2. The process according to claim 1, wherein the broken line rings having Xa, Xb, or Xc in the general formula (I) or (II) are independently a substituted or unsubstituted five- or six-membered heterocyclic ring having at least one to two nitrogen atoms, or a condensed ring thereof.

3. The process according to claim 1, wherein the trinucleus dye is a compound represented by the general formula (III) below or an isomer thereof in which the nitrogen atom in the central portion of the formula is at the 5-position instead of the 4-position:

where $r^8$, $r^9$, $r^{10}$, and $r^{11}$ are independently a hydrogen atom, a halogen atom, a substituted or unsubstituted alkyl group, an alkoxy group, a substituted or unsubstituted aryl group, or a substituted or unsubstituted amino group, and $r^8$ and $r^9$ may be bonded to each other to form a substituted or unsubstituted heterocyclic ring; $r^6$ independently in respective repeating units is absent or is an alkyl-substituted ethylene group, and is linked to $r^8$ or $r^9$ to form a ring; $r^1$ and $r^2$ are independently a substituted or unsubstituted aryl group, or $r^1$ and $r^2$ are bonded to each other to form a substituted or unsubstituted condensed ring; $r^3$, $r^4$, and $r^5$ are independently a hydrogen atom, a substituted or unsubstituted alkyl group, an alkylsulfonate group, a substituted or unsubstituted alkenyl group, a substituted or unsubstituted aryl group, or a substituted or unsubstituted aralkyl group; $X^1$ is an oxygen atom, a sulfur atom, a carbon atom, a nitrogen atom, or a selenium atom, and when $X^1$ is a carbon atom or a nitrogen atom, $X^1$ is bonded to any of hydrogen atoms, a substituted or unsubstituted alkyl group, a substituted or unsubstituted aryl group or a substituted or unsubstituted aralkyl group; $X^2$ is an oxygen atom, a sulfur atom, or a nitrogen atom, and when $X^2$ is a nitrogen atom, $X^2$ is bonded to any of a hydrogen atom, a substituted or unsubstituted alkyl group, a substituted or unsubstituted aryl, and a substituted or unsubstituted aralkyl group; $X^3$ is an oxygen atom or a sulfur atom; and m and e are independently an integer of from 0 to 3, not being simultaneously 0.

4. The process according to claim 1, wherein the trinucleus dye is a compound represented by the general formula (IV) below or an isomer thereof in which the nitrogen atom in the central portion of the formula is at the 5-position instead of the 4-position:

where $r^{19}$, $r^{20}$, and $r^{21}$ are independently a hydrogen atom, a halogen atom, a substituted or unsubstituted alkyl group, an alkoxy group, a substituted or unsubstituted aryl group, or a substituted or unsubstituted amino group, and $r^{19}$ and $r^{20}$ may be bonded to each other to form a substituted or unsubstituted condensed ring; $r^{12}$, $r^{13}$, $r^{14}$, and $r^{15}$ are independently a substituted or unsubstituted aryl, or $r^{12}$ and $r^{13}$ or $r^{14}$ and $r^{15}$ are bonded to each other to form a substituted or unsubstituted condensed ring; $r^{16}$, $r^{17}$, and $r^{18}$ are independently a hydrogen atom, a substituted or unsubstituted alkyl group, an alkylsulfonate group, a substituted or unsubstituted alkenyl group, a substituted or unsubstituted aryl group, or a substituted or unsubstituted aralkyl group; $X^4$ and $X^6$ are independently an oxygen atom, a sulfur atom, a carbon atom, a nitrogen atom, or a selenium atom, and when $X^4$ or $X^6$ is a carbon atom or a nitrogen atom, $X^4$ or $X^6$ is bonded to any of hydrogen atoms, a substituted or unsubstituted alkyl group, a substituted or unsubstituted aryl group, or a substituted or unsubstituted aralkyl group; $X^5$ is an oxygen atom, a sulfur atom or a nitrogen atom, and $X^5$ is a nitrogen atom, $X^5$ is bonded to any of a hydrogen atom, a substituted or unsubstituted alkyl group, a substituted or unsubstituted aryl, and a substituted or unsubstituted aralkyl group; $Z^-$ represents an anion; and y is an integer of 0, 1, or 2.

5. The process according to claim 1, wherein the trinucleus dye is selected from the structural formula (1), structural formula (2), structural formula (3), structural formula (4), structural formula (5) structural formula (6), structural formula (7), structural formula (8), structural formula (9), structural formula (10), structural formula (11) or structural formula (12):

(1)

(2)

(3)

(4)

-continued (5)

(6)

(7)

(8)

(9)

(10)

(11)

-continued

6. The process according to claim 1, wherein the biological substance of interest is an antibody or an antigen.

7. The process according to claim 1, wherein the biological substance of interest is a nucleic acid.

* * * * *

UNITED STATES PATENT AND TRADEMARK OFFICE
CERTIFICATE OF CORRECTION

PATENT NO. : 5,719,027

DATED : February 17, 1998

INVENTOR(S): TAKESHI MIYAZAKI ET AL.

It is certified that error appears in the above-identified patent and that said Letters Patent is hereby corrected as shown below:

[56] REFERENCES CITED

U.S. Patent Documents
"Waggonv et al." should read --Waggoner et al.--.

Foreign Patent Documents
"2191674" should read --2-191674--.

COLUMN 1

Line 56, "greater" should read --and the greater--.

COLUMN 3

Line 32, "structure" should read --structure;--.
Line 43, "groups," should read --group,--.

COLUMN 11

Line 66, "1/mol.cm." should read --1/mol·cm.--.

COLUMN 13

Line 40, "agent" should read --agents--.

COLUMN 14

Line 34, "substances" should read --substance--.

UNITED STATES PATENT AND TRADEMARK OFFICE
CERTIFICATE OF CORRECTION

PATENT NO. : 5,719,027

DATED : February 17, 1998

INVENTOR(S) : TAKESHI MIYAZAKI ET AL.

Page 2 of 2

It is certified that error appears in the above-identified patent and that said Letters Patent is hereby corrected as shown below:

<u>COLUMN 18</u>

Line 65, "dye" (first occurrence) should read --dye (--.

<u>COLUMN 23</u>

Line 9, "N$\underset{r^{18}}{|}$" (first occurrence) should read --N$\underset{r^{16}}{|}$--.

Signed and Sealed this

Eleventh Day of August 1998

Attest:

BRUCE LEHMAN

Attesting Officer        Commissioner of Patents and Trademarks